(12) United States Patent
McCarty, III

(10) Patent No.: US 10,743,981 B2
(45) Date of Patent: Aug. 18, 2020

(54) TENDON ANCHORING

(71) Applicant: L. Pearce McCarty, III, Orono, MN (US)

(72) Inventor: L. Pearce McCarty, III, Orono, MN (US)

(*) Notice: Subject to any disclaimer, the term of this patent is extended or adjusted under 35 U.S.C. 154(b) by 7 days.

(21) Appl. No.: 15/897,369

(22) Filed: Feb. 15, 2018

(65) Prior Publication Data

US 2018/0228597 A1 Aug. 16, 2018

Related U.S. Application Data

(60) Provisional application No. 62/459,900, filed on Feb. 16, 2017.

(51) Int. Cl.
*A61F 2/08* (2006.01)
*A61B 17/04* (2006.01)
*A61B 17/00* (2006.01)

(52) U.S. Cl.
CPC ........ *A61F 2/0811* (2013.01); *A61B 17/0401* (2013.01); *A61B 2017/0053* (2013.01); *A61B 2017/044* (2013.01); *A61B 2017/0409* (2013.01); *A61B 2017/0412* (2013.01); *A61B 2017/0414* (2013.01); *A61F 2002/0829* (2013.01); *A61F 2002/0852* (2013.01); *A61F 2002/0888* (2013.01)

(58) Field of Classification Search
CPC .. A61F 2/08; A61F 2/0811; A61F 2002/0817; A61F 2002/0823; A61F 2002/0841; A61F 2002/0852; A61F 2002/0858; A61F 2002/0829; A61B 17/0401; A61B 17/044; A61B 2017/0445; A61B 2017/0446; A61B 2017/0456
See application file for complete search history.

(56) References Cited

U.S. PATENT DOCUMENTS

| | | | |
|---|---|---|---|
| 5,258,016 A * | 11/1993 | DiPoto | A61B 17/0401 606/104 |
| 5,632,748 A | 5/1997 | Beck, Jr. et al. | |
| 5,702,397 A | 12/1997 | Goble et al. | |
| 5,984,927 A * | 11/1999 | Wenstrom, Jr. | A61B 17/0642 606/213 |
| 6,379,361 B1 | 4/2002 | Beck, Jr. et al. | |
| 6,517,542 B1 * | 2/2003 | Papay | A61B 17/0401 606/232 |
| 6,863,671 B1 * | 3/2005 | Strobel | A61F 2/0811 606/314 |
| 7,468,074 B2 | 12/2008 | Caborn et al. | |

(Continued)

FOREIGN PATENT DOCUMENTS

EP 2486856 7/2014

OTHER PUBLICATIONS

International Search Report in International Application No. PCT/US2016/029469, dated Aug. 8, 2016, 12 pages.

*Primary Examiner* — Alvin J Stewart
(74) *Attorney, Agent, or Firm* — Fish & Richardson P.C.

(57) ABSTRACT

Some embodiments described herein provide an improved tendon anchoring device and method for securing a muscle tendon to a bone. In particular, implementations described herein, the devices and methods are useful for anchoring a tendon to a bone in a patient's arm, including for example, anchoring a bicep tendon to bore formed in the targeted bone of the arm.

57 Claims, 12 Drawing Sheets

(56) References Cited

U.S. PATENT DOCUMENTS

| | | | |
|---|---|---|---|
| 7,572,283 B1 | 8/2009 | Meridew | |
| 8,048,158 B2* | 11/2011 | Hays | A61F 2/0811 606/151 |
| 8,512,405 B2 | 8/2013 | Baird | |
| 8,790,368 B2 | 7/2014 | Sullivan et al. | |
| 8,845,725 B2 | 9/2014 | Barwood et al. | |
| 10,080,646 B2* | 9/2018 | McCarty, III | A61F 2/0811 |
| 2001/0007074 A1* | 7/2001 | Strobel | A61B 17/8615 606/314 |
| 2002/0161401 A1* | 10/2002 | Steiner | A61B 17/0401 606/232 |
| 2003/0023268 A1* | 1/2003 | Lizardi | A61B 17/0401 606/232 |
| 2003/0100903 A1* | 5/2003 | Cooper | A61F 2/0811 606/300 |
| 2003/0105489 A1* | 6/2003 | Eichhorn | A61B 17/0401 606/232 |
| 2003/0153922 A1* | 8/2003 | Supinski | A61F 2/0811 623/13.14 |
| 2004/0059336 A1* | 3/2004 | Lombardo | A61F 2/0811 606/329 |
| 2004/0068262 A1* | 4/2004 | Lemos | A61F 2/0811 424/426 |
| 2004/0093031 A1* | 5/2004 | Burkhart | A61B 17/0401 606/232 |
| 2005/0075668 A1* | 4/2005 | Lizardi | A61B 17/0401 606/232 |
| 2005/0159812 A1* | 7/2005 | Dinger, III | A61F 2/0811 623/13.14 |
| 2006/0052787 A1* | 3/2006 | Re | A61F 2/0805 606/191 |
| 2006/0095130 A1* | 5/2006 | Caborn | A61F 2/0811 623/13.14 |
| 2006/0189991 A1* | 8/2006 | Bickley | A61B 17/864 606/916 |
| 2006/0247642 A1* | 11/2006 | Stone | A61B 17/0642 623/13.14 |
| 2007/0225805 A1* | 9/2007 | Schmieding | A61F 2/0811 623/13.14 |
| 2007/0270854 A1* | 11/2007 | Li | A61B 17/0401 606/232 |
| 2008/0154314 A1* | 6/2008 | McDevitt | A61F 2/0811 606/304 |
| 2008/0269743 A1* | 10/2008 | McNamara | A61B 17/0401 606/60 |
| 2008/0288069 A1* | 11/2008 | Wolf | A61B 17/0401 623/13.14 |
| 2008/0312700 A1* | 12/2008 | James | A61B 17/8625 606/304 |
| 2009/0112270 A1* | 4/2009 | Lunn | A61B 17/0401 606/301 |
| 2009/0287259 A1 | 11/2009 | Trenhaile et al. | |
| 2010/0016869 A1* | 1/2010 | Paulk | A61B 17/0401 606/144 |
| 2010/0063541 A1* | 3/2010 | Brunelle | A61B 17/0401 606/232 |
| 2010/0069958 A1* | 3/2010 | Sullivan | A61B 17/0401 606/232 |
| 2010/0145395 A1* | 6/2010 | Graf | A61F 2/0811 606/304 |
| 2011/0106252 A1* | 5/2011 | Barwood | A61F 2/0811 623/13.14 |
| 2011/0112558 A1 | 5/2011 | Whayne et al. | |
| 2012/0203340 A1* | 8/2012 | Choinski | A61F 2/0811 623/13.14 |
| 2013/0006278 A1 | 1/2013 | Mayer | |
| 2013/0261677 A1* | 10/2013 | Bouduban | A61B 17/0401 606/323 |
| 2014/0277130 A1* | 9/2014 | Housman | A61B 17/0401 606/232 |
| 2014/0303676 A1* | 10/2014 | Stroncek | A61B 17/8645 606/304 |
| 2015/0032157 A1 | 1/2015 | Dooney et al. | |
| 2015/0045886 A1* | 2/2015 | Miniaci | A61F 2/0811 623/13.14 |
| 2015/0142024 A1* | 5/2015 | Arai | A61F 2/0811 606/151 |
| 2015/0282801 A1* | 10/2015 | Arai | A61B 17/0401 606/232 |
| 2016/0270902 A1* | 9/2016 | Snedeker | A61B 17/0401 |
| 2016/0317282 A1* | 11/2016 | McCarty, III | A61F 2/0811 |
| 2016/0345954 A1* | 12/2016 | Marino | A61B 17/0401 |
| 2017/0189007 A1* | 7/2017 | Burkhart | A61B 17/0401 |
| 2017/0290655 A1* | 10/2017 | Piccirillo | A61F 2/0811 |
| 2017/0290656 A1* | 10/2017 | Piccirillo | A61B 17/8872 |
| 2018/0228597 A1* | 8/2018 | McCarty, III | A61F 2/0811 |
| 2018/0360438 A1* | 12/2018 | Curtis | A61B 17/0401 |
| 2018/0360592 A1* | 12/2018 | Arai | A61B 17/0466 |
| 2019/0038275 A1* | 2/2019 | Clark | A61B 17/0401 |
| 2019/0125420 A1* | 5/2019 | Diaz | A61B 17/866 |

\* cited by examiner

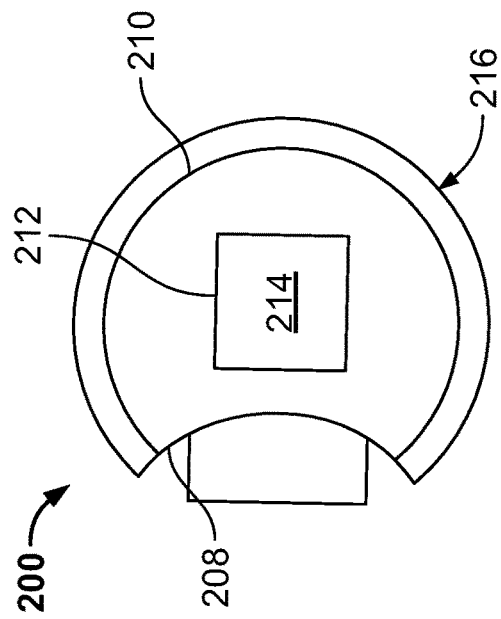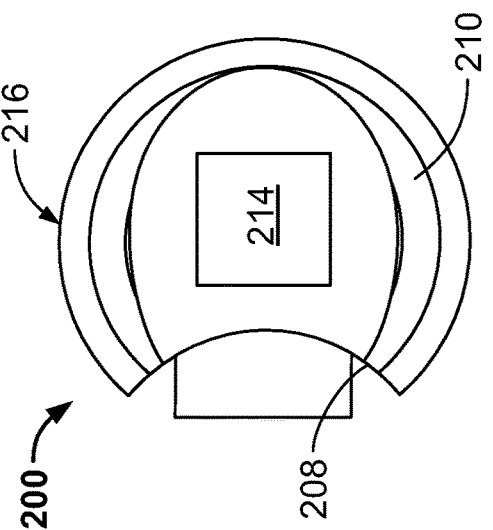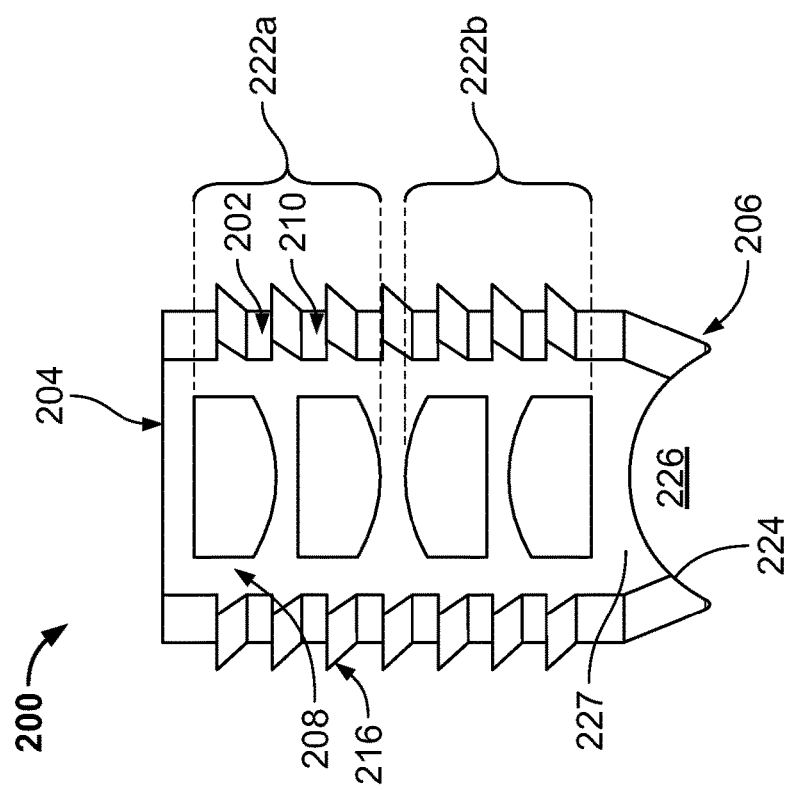

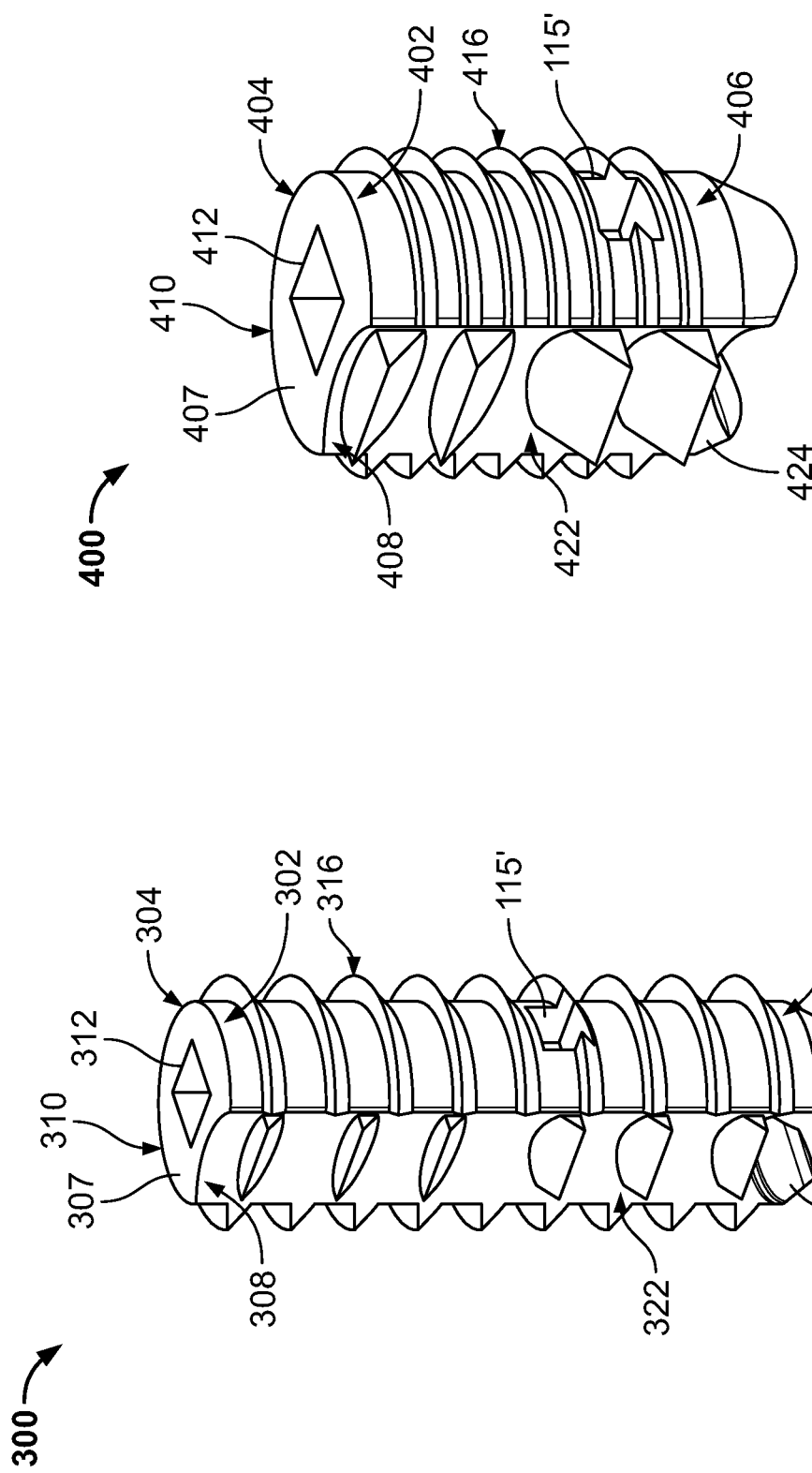

TENDON ANCHORING

CLAIM OF PRIORITY

This application claims priority to U.S. Provisional Application Ser. No. 62/459,900, filed on Feb. 16, 2017, the entire contents of which are hereby incorporated by reference.

TECHNICAL FIELD

This specification generally relates to implantable surgical devices, kits, and methods for anchoring tendon to bone.

BACKGROUND

Implantable surgical devices are often employed to achieve tendon fixation (or "anchoring") to bone without the necessity of complex suturing or other secondary fixation intermediaries. These types of devices are generally used in the context of tendon repair or "tenodesis" surgery. In the case of the former, such devices are used to reattach a tendon that has avulsed from its attachment. In the latter, the devices are used to attach or fix a tendon in a given location that achieves a specific therapeutic result for the patient. For example, in the case of a biceps tenodesis procedure, most commonly the long head of the biceps tendon is fixed to bone in either a proximal location within the bicipital groove or in a more distal location in order to reduce or eliminate pain coming from a damaged portion of the tendon.

SUMMARY

Some embodiments described herein provide an improved tendon anchoring device and method for securing a muscle tendon to a bone. In particular implementations described herein, the devices and methods are useful for anchoring a tendon to a bone in a patient's arm, including for example, anchoring a bicep tendon to a tunnel formed in the targeted bone of the arm. Optionally, the tendon anchoring device is configured to provide improved mechanical stability both during and after insertion into the bone, to provide improved mating with an insertion tool while avoiding interference from other components, to provide improved anchoring strength after the device secures the tendon into the bone, to provide improved opportunity for an optimized biologic healing environment by maximizing the surface of the tendon to be anchored with the target bone, to provide an improved process by which the tendon is secured to the bone by making the process more rapid and efficient, or a combination thereof.

In one aspect, a tendon anchoring device disclosed herein features an elongated body extending between a first end and a second end, the body comprising at least one concave side wall and at least one convex side wall, the concave and convex side walls extending longitudinally between the first and second ends; a tool engagement surface at the first end of the body adapted to accommodate a mating surface of an insertion tool; a tendon engagement surface at the second end of the body, the tendon engagement surface defining an archway bounded by overhanging portions of the convex side wall; a plurality of anchor ribs projecting laterally from the convex side wall and distributed between the first and second ends of the body, each of the anchor ribs engageable with a wall formed along a tunnel of a bone; and a plurality of support ribs projecting laterally from the concave side wall and distributed between the first and second ends of the body, each of the support ribs engageable with a tendon residing within the archway of the tendon engagement surface.

In some embodiments, the concave side wall can be contiguous to the convex side wall, the concave and convex sidewalls defining the lateral boundary of the body. The concave side wall can constitute the only concave portion of the lateral boundary of the body. In some embodiments, the convex side wall defines a substantially circular cross-section. In some embodiments, the tendon engagement surface can meet the concave side wall at a first arcuate edge, and wherein the archway extends across the body to meet a portion of the convex side wall at a second arcuate edge. In some embodiments, the body can further comprise an interior throughbore extending between the first and second ends of the body. In some embodiments, the throughbore can be sized to receive at least a portion of a suture thread. In some embodiments, the throughbore can extend from an opening at the first end of the body, the opening shaped to accommodate a portion of the insertion tool in an interlocking engagement. In some embodiments, the throughbore can define a rectangular cross-section. In some embodiments, the throughbore can comprise no more than 20% of the cross-sectional area of the body. In some embodiments, one or more of the support ribs can be longitudinally canted relative to a transverse plane of the body. In some embodiments, a first set of the support ribs can be canted at a first angle relative to the transverse plane and a second set of the support ribs are canted at a second angle that is different from the first. In some embodiments, at least one of the anchor ribs can include an annular, inverse-frustum-shaped structure circumscribing the convex side wall. In some embodiments, the plurality of anchor ribs can be spaced apart from one another at regular intervals along the convex side wall. In some embodiments, the body can further comprises an aperture located on the convex side wall sized to receive at least a portion of a suture thread. In some embodiments, the aperture can extend through the convex side wall to intersect a longitudinal interior throughbore of the body. In some embodiments, the body can comprise first and second apertures aligned on opposing locations of the convex side wall to form a passageway extending across the body. In some embodiments, the body can comprise an integral, monolithic structure comprising a material selected from the group consisting of: poly ether ether ketone, poly-L-lactic acid, titanium, and stainless steel.

In a second aspect, a method for coupling a tendon to a bone can include forming a tunnel in a bone, the tunnel comprising an opening and a wall circumscribing the opening; placing a tendon over the opening of the tunnel; placing a tendon anchoring device over the opening and at least a portion of the tendon; aligning the tendon engagement surface with the tendon to place the tendon within the archway; and placing the anchoring device carrying the tendon into the tunnel through the opening, thereby causing the anchor ribs to engage the wall of the tunnel and the support ribs to support the tendon against the wall of the tunnel. The anchoring device in any of the methods provided herein can include an elongated body comprising at least one concave side wall and at least one convex side wall extending longitudinally between first and second ends of the body; a tool engagement surface at the first end of the body; a tendon engagement surface at the second end of the body, the tendon engagement surface defining an archway bounded by overhanging portions of the convex side wall; a plurality of anchor ribs projecting laterally from the convex side wall; and a plurality of support ribs projecting laterally from the concave side wall;

In some embodiments, concave side wall of the anchoring device can be contiguous to the convex side wall, the concave and convex sidewalls defining the lateral boundary of the body. In some embodiments, the concave side wall of the anchoring device can constitute the only concave portion of the lateral boundary of the body. In some embodiments, the convex side wall of the anchoring device can define a substantially circular cross-section. In some embodiments, the tendon engagement surface of the anchoring device can meet the concave side wall at a first arcuate edge, and wherein the archway extends across the body to meet a portion of the convex side wall at a second arcuate edge. In some embodiments, the body of the anchoring device further can include an interior throughbore extending between the first and second ends of the body. In some embodiments, the throughbore can be sized to receive at least a portion of a suture thread. In some embodiments, the throughbore can extend from an opening at the first end of the body, the opening shaped to accommodate a portion of the insertion tool in an interlocking engagement. In some embodiments, the throughbore can define a rectangular cross-section. In some embodiments, the throughbore can be no more than 20% of the cross-sectional area of the body. In some embodiments, one or more of the support ribs of the anchoring device can be longitudinally canted relative to a transverse plane of the body. In some embodiments, a first set of the support ribs can be canted at a first angle relative to the transverse plane and a second set of the support ribs can be canted at a second angle that is different from the first. In some embodiments, at least one of the anchor ribs of the anchoring device can include an annular, inverse-frustum-shaped structure circumscribing the convex side wall. In some embodiments, the plurality of anchor ribs of the anchoring device can be spaced apart from one another at regular intervals along the convex side wall. In some embodiments, aligning the tendon engagement surface with the tendon can include: routing a suture thread through at least a portion of an interior bore of the body of the anchoring device; and routing the suture thread around the tendon. In some embodiments, routing the suture thread through the interior bore can include inserting the suture thread through an opening at the tool engagement surface of the anchoring device. In some embodiments, routing the suture thread through the interior bore can include inserting the suture thread through an opening at the convex side wall of the anchoring device. In some embodiments, aligning can further include pulling two opposing end portions of the suture thread to urge the tendon against the tendon engagement surface. In some embodiments, the method can further include, prior to forcing the anchoring device into the tunnel, securing the suture thread to a cleat located on an insertion tool coupled to the anchoring device. In some embodiments, placing the anchoring device into the tunnel can include engaging an insertion tool with the anchoring device by placing a tip of the insertion tool within an interior bore of the anchoring device; and placing a flange of the insertion tool against the tool engagement surface of the anchoring device; and applying a force to the insertion tool.

In a third aspect, a surgical kit provided herein can include a tendon anchoring device and an insertion tool. The tendon anchoring device can include an elongated body extending between a first end and a second end, the body comprising at least one concave side wall and at least one convex side wall, the concave and convex side walls extending longitudinally between the first and second ends; a tool engagement surface at the first end of the body; a tendon engagement surface at the second end of the body, the tendon engagement surface defining an archway bounded by overhanging portions of the convex side wall; a plurality of anchor ribs projecting laterally from the convex side wall and distributed between the first and second ends of the body, each of the anchor ribs engageable with a wall formed along a tunnel of a bone; and a plurality of support ribs projecting laterally from the concave side wall and distributed between the first and second ends of the body, each of the support ribs engageable with a tendon residing within the archway of the tendon engagement surface. The insertion tool can be adapted to interface with the tool engagement surface of the anchoring device and facilitate insertion of the anchoring device into the tunnel of the bone.

In some embodiments, the concave side wall of the anchoring device can be contiguous to the convex side wall, the concave and convex sidewalls defining the lateral boundary of the body. In some embodiments, the concave side wall of the anchoring device can constitute the only concave portion of the lateral boundary of the body. In some embodiments, the convex side wall of the anchoring device can define a substantially circular cross-section. In some embodiments, the tendon engagement surface of the anchoring device can meet the concave side wall at a first arcuate edge, and wherein the archway extends across the body to meet a portion of the convex side wall at a second arcuate edge. In some embodiments, the body of the anchoring device can further comprise an interior throughbore extending between the first and second ends of the body. In some embodiments, the throughbore can be sized to receive at least a portion of a suture thread. In some embodiments, the throughbore can extend from an opening at the first end of the body, the opening shaped to accommodate a portion of the insertion tool in an interlocking engagement. In some embodiments, the throughbore can define a rectangular cross-section. In some embodiments, the throughbore can comprise no more than 20% of the cross-sectional area of the body. In some embodiments, one or more of the support ribs of the anchoring device can be longitudinally canted relative to a transverse plane of the body. In some embodiments, a first set of the support ribs can be canted at a first angle relative to the transverse plane and a second set of the support ribs are canted at a second angle that is different from the first. In some embodiments, at least one of the anchor ribs of the anchoring device can include an annular, inverse-frustum-shaped structure circumscribing the convex side wall. In some embodiments, the plurality of anchor ribs of the anchoring device can be spaced apart from one another at regular intervals along the convex side wall. In some embodiments, the body of the anchoring device can further comprise an aperture located on the convex side wall sized to receive at least a portion of a suture thread. In some embodiments, the aperture can extend through the convex side wall to intersect a longitudinal interior throughbore of the body. In some embodiments, the body can comprise first and second apertures aligned on opposing locations of the convex side wall to form a passageway extending across the body. In some embodiments, the body of the anchoring device can include an integral, monolithic structure comprising a material selected from the group consisting of: poly ether ether ketone, poly-L-lactic acid, titanium, and stainless steel. In some embodiments, the insertion tool can include a cleat for securing a suture thread wrapped around a tendon and the anchoring device. In some embodiments, the anchoring device can include an interior throughbore extending between the first and second ends of the body, and wherein the insertion tool comprises a tip configured to engage the interior throughbore to couple the insertion tool to the anchoring device. In some embodiments, the tip of the insertion tool and the throughbore of the anchoring device can be configured to provide an interlocking engagement. In some embodiments, the tip of the insertion tool can have a rectangular cross-section. In some embodiments, the insertion tool can include a flange for interfacing with the tool engagement surface of the anchoring device, the interface sufficient to transfer force applied to the insertion tool to the anchoring device. In some embodiments, the lateral boundary of the flange can be larger than that of the tool engagement surface.

In a fourth aspect, a tendon anchoring device provided herein can include a body extending between a first end and a second end, the body comprising a concave side wall and a convex side wall, the concave and convex side walls extending between the first and second ends; a tool engagement surface at the first end of the body; a tendon engagement surface at the second end of the body; a plurality of anchor ribs projecting from the convex side wall and distributed between the first and second ends of the body; and a plurality of support ribs projecting from the concave side wall and distributed between the first and second ends of the body.

In a fifth aspect, a method for coupling a tendon to a bone provided herein can include placing a tendon over an opening of a tunnel in a bone, the tunnel comprising an opening and a wall circumscribing the opening; placing a tendon anchoring device over the opening and at least a portion of the tendon; aligning the tendon engagement surface with the tendon; and placing the anchoring device carrying the tendon into the tunnel through the opening, thereby causing the anchor ribs to engage the wall of the tunnel and the support ribs to support the tendon against the wall of the tunnel. The anchoring device of the method can include a body comprising a concave side wall and a convex side wall extending between first and second ends of the body; a tool engagement surface at the first end of the body; a tendon engagement surface at the second end of the body; a plurality of anchor ribs projecting laterally from the convex side wall; and a plurality of support ribs projecting laterally from the concave side wall.

In a sixth aspect, a tendon anchoring device for securing a tendon to a bone can include a body extending between a first end and a second end, the body comprising a central bore extending between the first end and the second end, a concave side wall and a convex side wall, the concave and convex side walls extending between the first and second ends; a tool engagement cavity at the first end of the body for mating with a tip of an insertion tool, the tool engagement cavity being defined by a proximal portion of the central bore; a tendon engagement surface at the second end of the body; and at least one side aperture in the convex side wall for receiving a suture tethered to a tendon, wherein the side aperture is spaced apart from the tool engagement cavity.

In a seventh aspect, a tendon anchoring device for securing an a tendon to a bone, can include a body extending between a first end and a second end, the body comprising a concave side wall and a convex side wall that both extend between the first and second ends, and a four-sided bore extending between the first end and the second ends; wherein at least a proximal portion of the four-sided bore defines a tool engagement cavity at the first end of the body for mating with a tip of an insertion tool.

The details of one or more implementations of the subject matter described in this specification are set forth in the accompanying drawings and the description below. Other features, aspects, and advantages of the subject matter will become apparent from the description, the drawings, and the claims.

BRIEF DESCRIPTION OF THE DRAWINGS

FIG. 10 is rear view of the second example tendon anchoring device.

FIG. 11 is a top view of the second example tendon anchoring device.

FIG. 12 is a bottom view of the second example tendon anchoring device.

FIG. 13 is a perspective view of a third example tendon anchoring device.

FIG. 14 is a perspective view of a fourth example tendon anchoring device.

Certain aspects of the drawings may be exaggerated to better show the features, process steps, and results. Like reference numbers and designations in the various drawings may indicate like elements.

DETAILED DESCRIPTION

Figure 1:
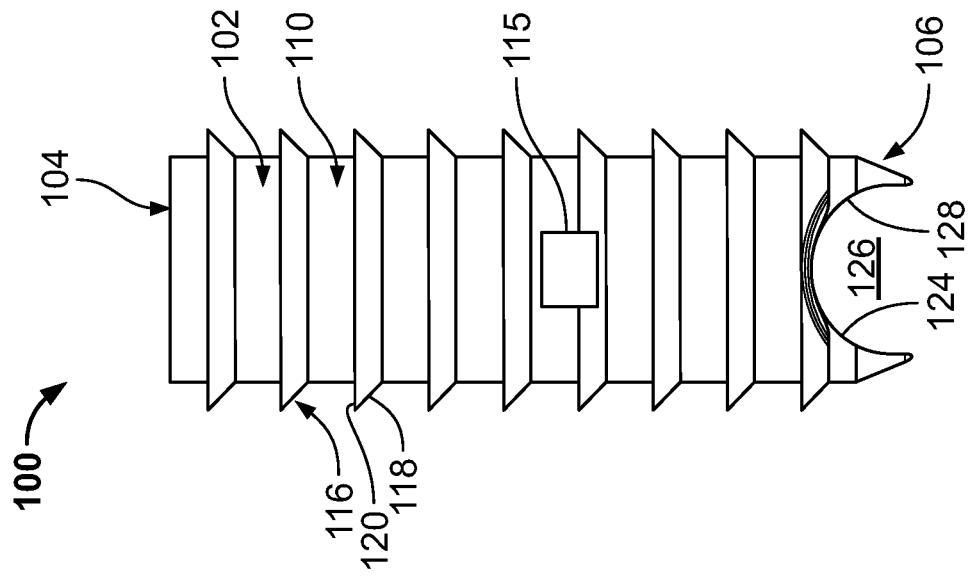
FIG. 1 is a perspective view of a first example tendon anchoring device.
Figure 2:
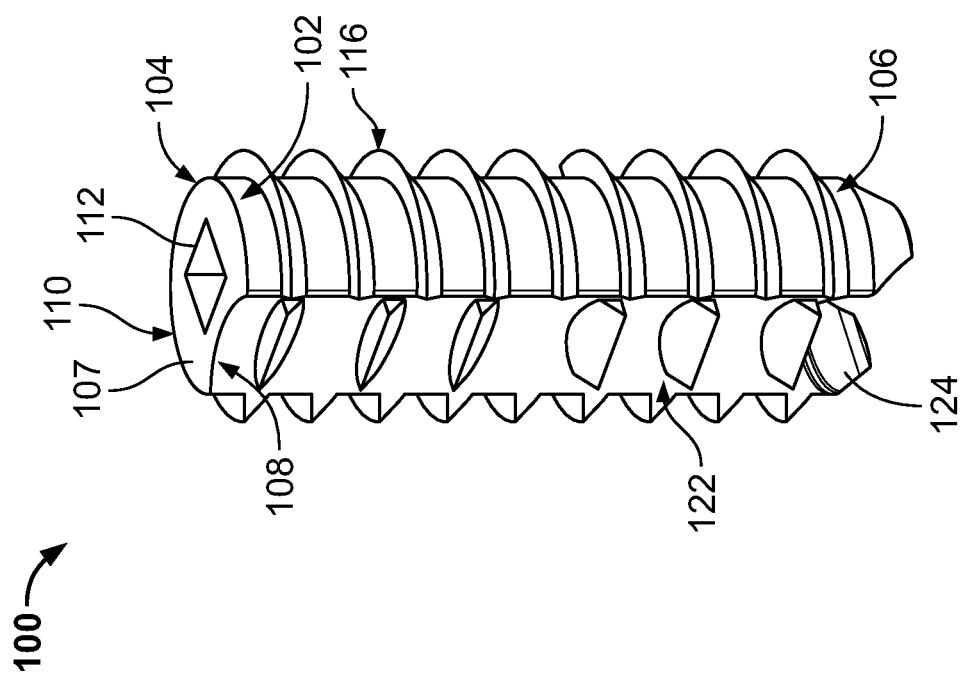
FIG. 2 is a front view of the first example tendon anchoring device.
Figure 4:
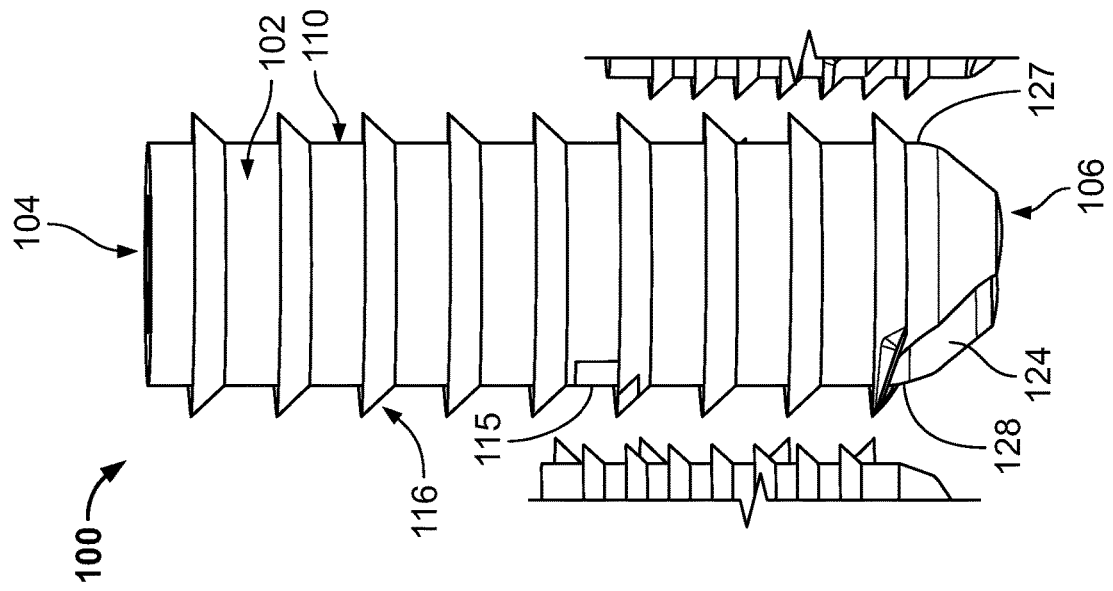
FIG. 4 is side view of the first example tendon anchoring device.
Figure 3:
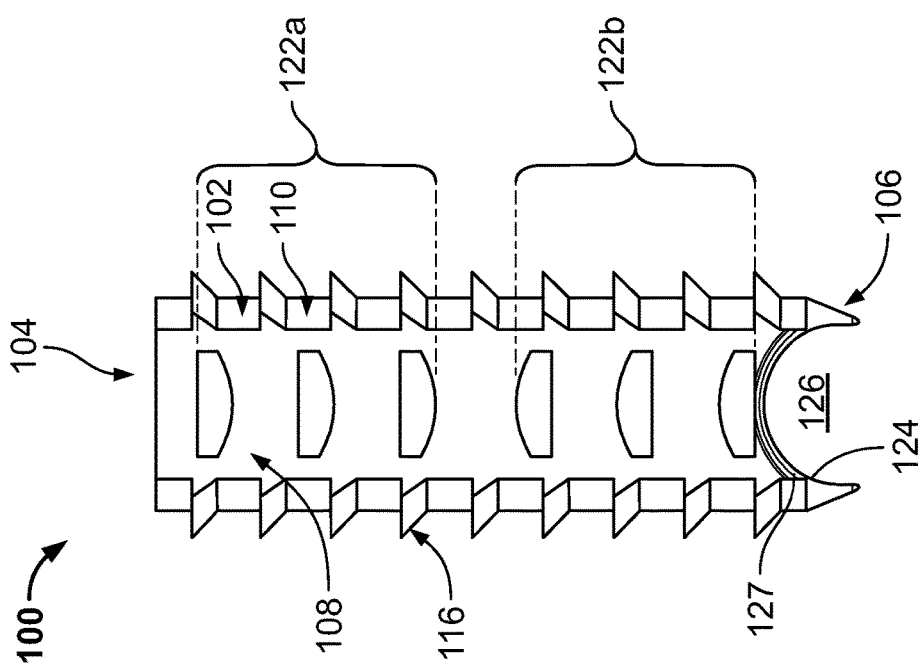
FIG. 3 is a rear view of the first example tendon anchoring device.
Figure 7:
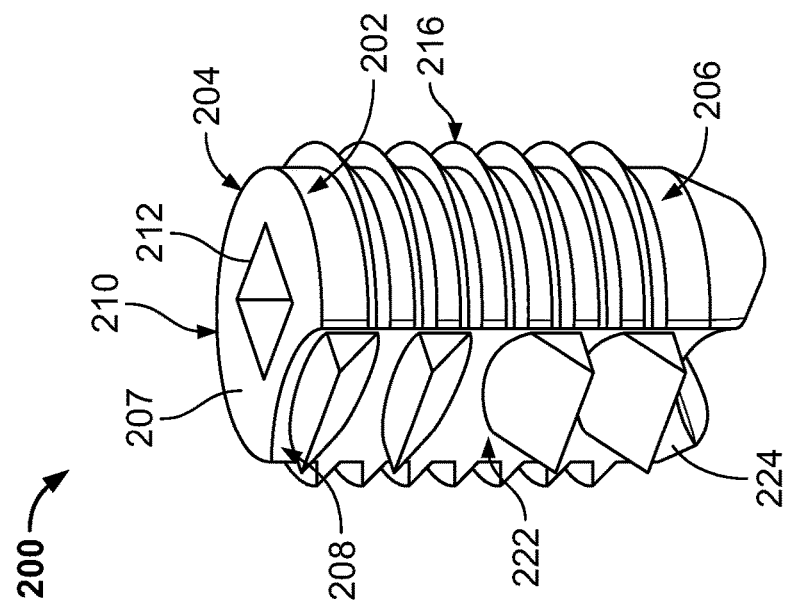
FIG. 7 is a perspective view of a second example tendon anchoring device.
Figure 5:
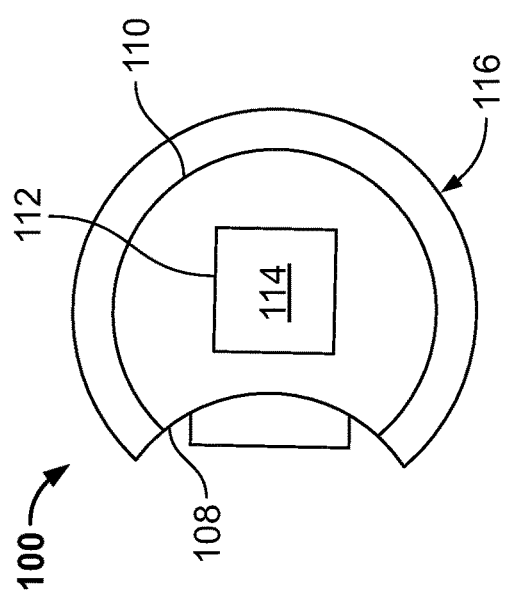
FIG. 5 is a top view of the first example tendon anchoring device.
Figure 6:
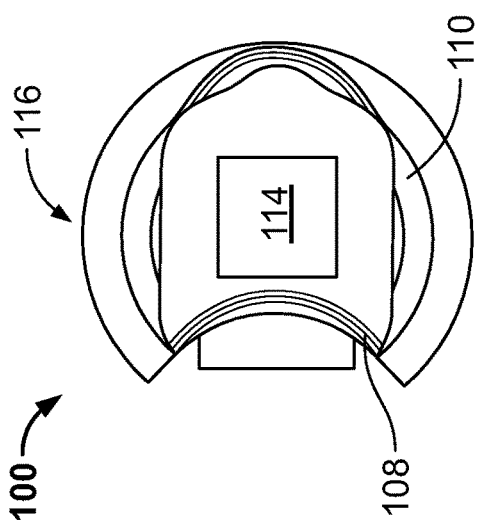
FIG. 6 is a bottom view of the second example tendon anchoring device.
Figure 9:
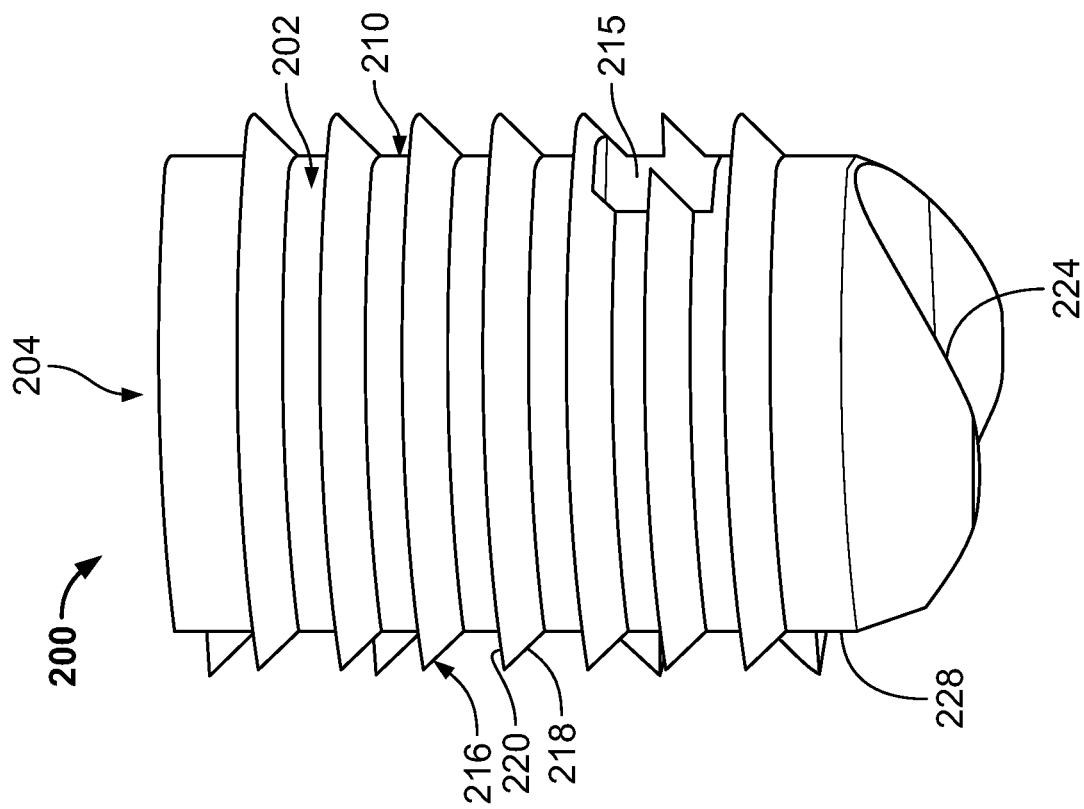
FIG. 9 is a side view of the second example tendon anchoring device.
Figure 8:
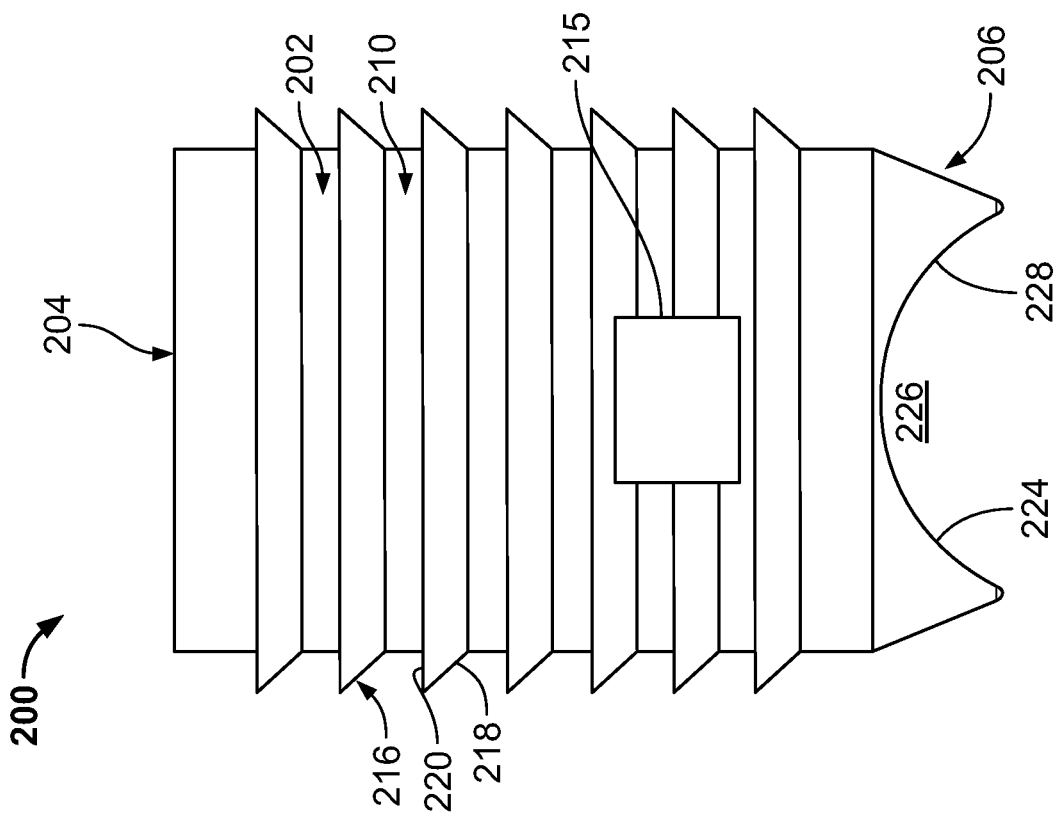
FIG. 8 is a front view of the second example tendon anchoring device.

Referring to FIGS. 1-6, a first example tendon anchoring device 100 includes an elongated body 102 extending between a first (top or proximal) end 104 and a second (bottom or distal) end 106. In this example, the top end 104 has a substantially flat tool engagement surface 107 and non-circular opening 112 that mate with an insertion tool (e.g., tool 500 of FIGS. 16-20) used for implanting the anchoring device 100. The lateral boundary of the body 102 is defined by an outer surface including a concave side wall 108 and a convex side wall 110. In this embodiment, the concave and convex side walls 108,110 join together at both ends and extend longitudinally between the top and bottom ends 104,106 of the body 102.

In this example, the concave and convex side walls 108,110 are substantially straight in the longitudinal direction, giving the body 102 a generally cylindrical appearance with a concave face therein. In this example, the concave and convex side walls 108,110 are contiguous to one another, forming a complete uninterrupted lateral boundary of the body 102. In this example, the convex side wall 110 constitutes the majority of the lateral boundary (e.g., about 75%) of the body 102. In this example, the convex side wall 110 bows inward from the circumference of the substantially circular concave side wall 108. Of course, various other implementations may involve anchor bodies having substantially different shapes, sizes, and relative dimensions without departing from the scope of the present disclosure. However, the particular design shown and described in this example has exhibited strong performance characteristics in terms of structural integrity, ease of implantation, and anchoring tenacity. For instance, in some circumstances, it may be advantageous to provide a single concave side wall 108 (e.g., as opposed to two or more) to increase the effective thickness and column strength of the device 100, which results in higher resistance to buckling during implantation into bone. The inclusion of a single concave side wall 100 provides an ideal balance between mechanical strength during the impaction process, implant purchase, and/or fixation within a prepared bony bore and optimization of a biological healing environment by prevention of strangulation or over—compression of a tendon that would occur with a fully cylindrical implant having total circumference contact with the tendon. As the device 100 is designed under typical circumstances to receive the tendon along both apposing convex and concave aspects along the length of the implant, the convex aspect of the external diameter of the device 100 permits a secure, line-to-line fit for the implant around the majority of the circumference of the prepared bore, while the inclusion of a single concavity running the length of one side of the device 100 provides an opportunity for the tendon to run in a "channel" that provide secure, but reduced compression that could favor preservation of vascularity and other biological properties conducive to healing. This differs markedly from other fixation architectures, such as that provided by an interference screw, which typically has the tendon running only along one side of the device 100 and which compresses the tendon against a fully circumferential convex surface, potentially compromising vascularity and other biological properties conducive to healing.

The body 102 of tendon anchoring device 100 further includes the opening 112 in the flat tool engagement surface 107 of top end 104. The opening 112 leads to a throughbore 114 extending from the top end to the bottom end 106. The top and bottom ends 104,106 can have a filleted edge (or chamfer) to prevent or reduce tissue damage to the tendon during or after device implantation. In this example, the opening 112 and the bore 114 share a 4-sided cross-section (e.g., square, rectangular, or the like), and the cross-section of the bore 114 remains substantially constant throughout its axial length. At least the distal portion of the bore 114 is sized and shaped to optionally receive a suture (e.g., looped around or connected with a tendon) for securing the tendon to the anchoring device 100. At least the proximal portion of the bore 114 and the proximal opening 112 are also sized and shaped to mate with the non-circular tip of an insertion tool (e.g., tool 500 of FIGS. 16-20). The insertion tool is not limited to only non-circular tips, and, in some embodiments, can include a semi-circular or a fully circular tip portion. In some examples, the shape and size of the bore 114 may be appropriately limited to maintain the structural integrity of the tendon anchoring device 100. Accordingly, in some examples, the cross-sectional area of the bore 114 is no more than about 20% of the cross-sectional area of the solid portion of the body 102 (e.g., between about 15% and 18%, or about 16%).

The body 102 of the tendon anchoring device 100 still further includes an aperture 115 located on the convex side wall 110 at the front of the device, opposite the concave side wall 108. The aperture 115 extends entirely through the convex side wall 110 to intersect the bore 114. Similar to the bore 114, the aperture 115 is appropriately adapted to receive a portion of the aforementioned optional suture for securing the tendon to the anchoring device 100. The aperture 115 can include beveled edges to reduce the risk of suture laceration during the device implantation. Accordingly, as described below with reference to FIGS. 21-27, the aperture 115 can be used when a surgeon is routing the suture through the bore 114 and around (or through) the tendon, thereby tethering the targeted portion of the tendon to the distal end of the device 100 prior to impacting the device 100 into the bone. In some circumstances, introducing the suture to the bore 114 through the aperture 115 may be significantly easier than threading the suture through the top opening 112. Moreover, the side aperture 115 can be advantageous because it may reduce the likelihood of interference between the suture and the insertion tool tip within the bore 114. Even further, routing the suture through the aperture 115 may increase the anchoring strength of the device because the suture material exiting the aperture is wedged between the exterior of the convex wall 110 and the opposing wall of the bone tunnel during implantation, forming a self-tightening construct that further draws and secures the tendon to the distal, convex tip of the implant.

In some examples, the body 102, and potentially one or more additional components of the tendon anchoring device 100 (e.g., the ribs described below), can be fabricated as an integral, monolithic (one-piece) structure. In some examples, one or more components of the tendon anchoring device 100, including the body 102, can be fabricated using one or more biocompatible materials. Some exemplary materials may include, but are not limited to: poly ether ether ketone (PEEK) and similar plastics, poly-L-lactic acid (PLLA) or isomer with varying additions consisting of calcium, phosphate and other materials known to be compatible with human bone, and similar bioabsorbable or biocomposite materials, titanium and various stainless steel alloys.

Still referring to FIGS. 1-6, the tendon anchoring device 100 further includes a plurality of anchor ribs 116 projecting laterally from the convex side wall 110. The anchor ribs 116 are distributed longitudinally along the convex side wall 110 between the top and bottom ends 104,106 of the body 102. Each of the anchor ribs 116 is designed to engage the wall of a tunnel formed in a patient's bone. In particular, the anchor ribs 116 can be configured to facilitate a friction fit between the tendon anchoring device 100 and the bone tunnel. For instance, in this example, each of the anchor ribs 116 is provided in the form of an annular, inverse-frustum-shaped structure that circumscribes the convex side wall 110. The inverse-frustum shape allows the anchor ribs 116 to be urged into the bone tunnel with significantly less force than is required to remove them from the tunnel. More specifically, the slanted lower surface 118 of the anchor ribs 116 facilitates a downward sliding motion against the side wall of the bone tunnel that enables insertion of the bone anchoring device 100. Conversely, the substantially flat upper surface 120 resists sliding in the upward direction to inhibit removal of the device. In this example, the tendon anchoring device 100 includes nine anchor ribs 116 spaced apart from one another at regular intervals along the length of the convex side wall 110. In alternative embodiments, the number, shape, size, orientation, and distribution of anchor ribs 116 may be different than the depicted embodiment.

The tendon anchoring device 100 still further includes a plurality of support ribs 122 projecting laterally from the concave side wall 108. Like the anchor ribs 116, the support ribs 122 are distributed longitudinally along the concave side wall between the top and bottom ends 104,016 of the body 102. Each of the support ribs is designed to engage and non-destructively support the tendon carried by the anchoring device 100. In this example, the six support ribs 122 are divided into two sets—a first set of three ribs 122a proximate the top end 104 of the body 102 that are canted at an upward angle relative to a transverse plane of the device, and a second set of three ribs 122b proximate the bottom end 106 that are canted at a downward angle relative to the transverse plane. This variation in angulation of the ribs provides substantial interference-based resistance to tendon motion at the implant-tendon interface after implantation. Furthermore, opposing orientation of the interference ribs, which can be oriented at 180 degrees from one another), allows for a variety of tendon-implant orientation constructs without compromising fixation strength. In some circumstances, the implant orientation construct can include, but is not limited to, one in which the single concave wall of the implant faces a line of pull of the muscle attached to the tendon and another in which the single concave wall of the implant faces opposite the line of pull of the muscle attached to the tendon being fixed. Again, in alternative embodiments, the number, shape, size, orientation, and distribution of support ribs 122 may be different that the depicted embodiment.

The anchoring device 100 further includes a tendon engagement surface 124 at the bottom end 106 of the body 102. The tendon engagement surface 124 has an arcuate profile, defining an upwardly concave archway 126 bounded by overhanging portions of the convex side wall 110. The tendon engagement surface 124 meets the concave side wall 108 at a first edge 127 and the convex side wall 110 at a second edge 128, such that the archway 126 extends across the entire width of the body 102. The shape and size of the tendon engagement surface 124 are prescribed to accommodate the anchored tendon.

The tendon engagement surface 124 is adapted to provide substantial functionality that allows the anchoring device 100 to anchor the tendon without the use of sutures, when desired. In particular, the arcuate, concave profile of the distal end of the anchoring device 100 is adapted to maneuver and manipulate the tendon into the prepared bore in the host bone by pinning the tendon within the concave distal tip and moving the tendon in a desired direction. In some embodiments, the concave distal tip of the implant can include projections, fins or fibs (not shown) that further facilitate manipulation of a tendon without the use of suture for purposes of centering the tendon over the prepared bore prior to impaction and fixation of the implant.

FIGS. 7-12 depict a second example tendon anchoring device 200 that is similar to device 100 described above. This second example anchoring device 200 is similar to the first example (e.g., device 100) in terms of structural elements, but is scaled down to a smaller size. For example, the anchoring device 200 is significantly shorter in length than the anchoring device 100. Accordingly, instead of nine anchor ribs 116 and six support ribs 122, the anchoring device 200 includes seven anchor ribs 116 and four support ribs 122. In certain embodiments the anchor may be scaled smaller or larger than illustrated depending upon the scale of the tendon to be fixed and the osseous anatomy of the target site. For example, a tendon targeted in the hand or wrist area would require an even smaller scale implant than illustrated, but with the same functionality and design elements.

FIGS. 13 and 14 depict third and fourth example tendon anchoring devices 300,400 that correspond substantially to the respective first and second example anchoring devices 100,200. The anchoring devices 300 and 400 differ from the prior examples in that the aperture 115 is located on the convex side wall 110 at a flank of the device, as opposed to the front. Further, the anchoring devices 300 and 400 further include an additional aperture 115' located on the opposing flank to a form a lateral passageway 130 intersecting the bore 114. Accordingly, in some embodiments, the tendon anchoring device 300, 400 can be equipped with a pair of opposing apertures 115 and 115' in a longitudinal plane of the device 300, 400 passing through opposing sides of the convex sidewall 110 (e.g., not through the concave sidewall 108). Similar to the previously described examples, the apertures 115 and 115' sized and shaped to receive respective portions of the aforementioned suture for securing the tendon to the anchoring device 300, 400. Accordingly, as described below with reference to FIGS. 21-27, the apertures 115 and 115' can be used when a surgeon is routing the suture through the bore 114 and around the tendon, thereby tethering the targeted portion of the tendon to the distal end of the device 100 prior to impacting the device 100 into the bone. As such, the device configuration may reduce the likelihood of interference between the suture and the insertion tool tip within the bore 114. Moreover, routing the suture through the opposing apertures 115 and 115' can significantly increase the anchoring strength of the device 300, 400 because each end of suture length exiting the apertures 115 and 115' is wedged between the exterior of the convex wall 110 and the opposing wall of the bone tunnel during implantation as explained previously.

Figures 15, 16:
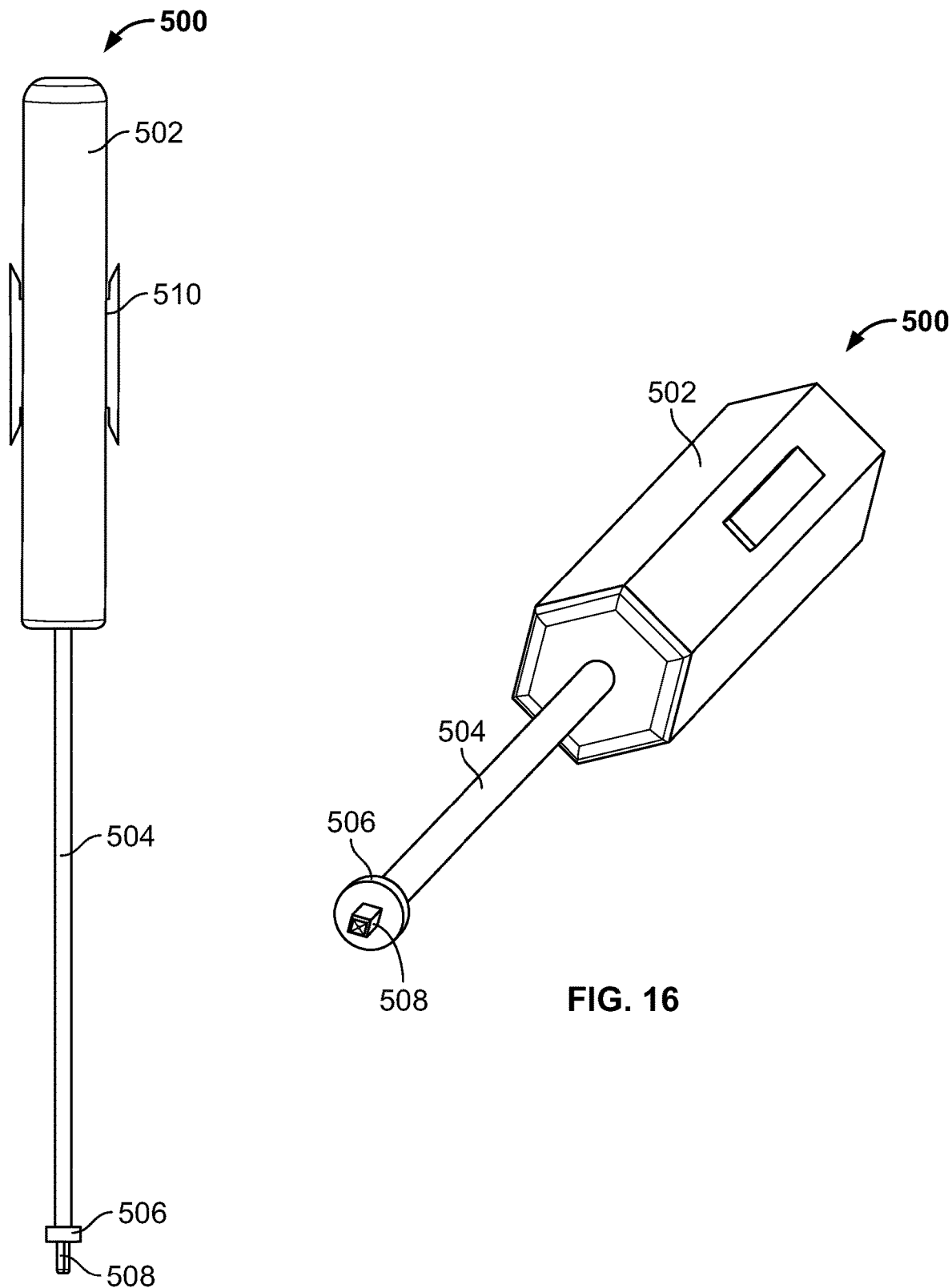
FIG. 15 is a side view of an insertion tool.
FIG. 16 is a perspective view of the insertion tool.

Referring next to FIGS. 15 and 16, an insertion tool 500 for facilitating implantation of the tendon anchoring devices 100,200,300,400 includes a handle 502, a shaft, 504, a flange 506, and a distal tip 508. The handle 502 is appropriately sized to be grasped and manipulated by a human hand during a surgical procedure (though a machine or mechanical device could also be used). Further, the handle 502 includes cleats 510 on opposing side surfaces thereof. As discussed below, the cleats 510 are provided to secure suture material routed through the anchoring device and around the tendon to hold the tendon in place against the device during implantation in the event that a suture is utilized. The elongated shaft 504 extends longitudinally from the handle 502, leading to the flange 506 and distal tip 508. The tip 508 has a rectangular (e.g., square) cross-section matching that of the opening 112 and bore 114 of the anchoring device 100. The non-circular cross-sections of these components creates an interlocking engagement between the insertion tool 500 and anchoring device that inhibits relative rotational movement between them. In some examples, the tip 508 of the insertion tool 500 is press fit into the bore 114 of the anchoring device. In some other examples, the tip of the insertion tool and the bore of the device are circular and provided with mating threads to facilitate an interlocking engagement. The rectangular shaped tip, however, may be particularly advantageous in certain implementations because it is relatively simple to manufacture compared to rounded or irregularly shaped tips or threaded tips.

When the tip 508 of the insertion tool 500 projects into the bore 114 of the anchoring device 100, the flange 506 is seated against the flat tool engagement surface 107. This arrangement facilitates a transfer of downward force from the insertion tool 500 to the anchoring device 100 to urge the device into the bone tunnel during implantation. In some examples, the flange 506 is at least semi-transparent (e.g., translucent), which allows visualization of the anchoring device 100 arthroscopically as it is seated flush with the bone structure. In some examples, the lateral boundary of the flange 506 is larger than that of the anchoring device 100 and the recipient bone tunnel. The portion of the flange 506 overhanging the tendon anchoring device 100 and bone tunnel may provide a "positive stop" that inhibits inadvertent over-insertion of the device, providing additional, important functionality.

Figure 18:
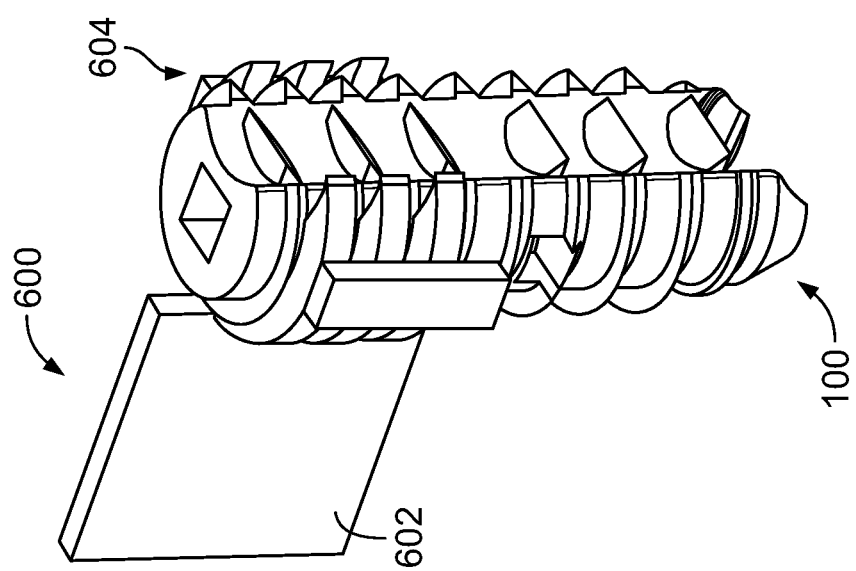
FIGS. 17-20 are progressive perspective views illustrating a technique for pre-loading a tendon anchoring device onto an insertion tool.
Figure 17:
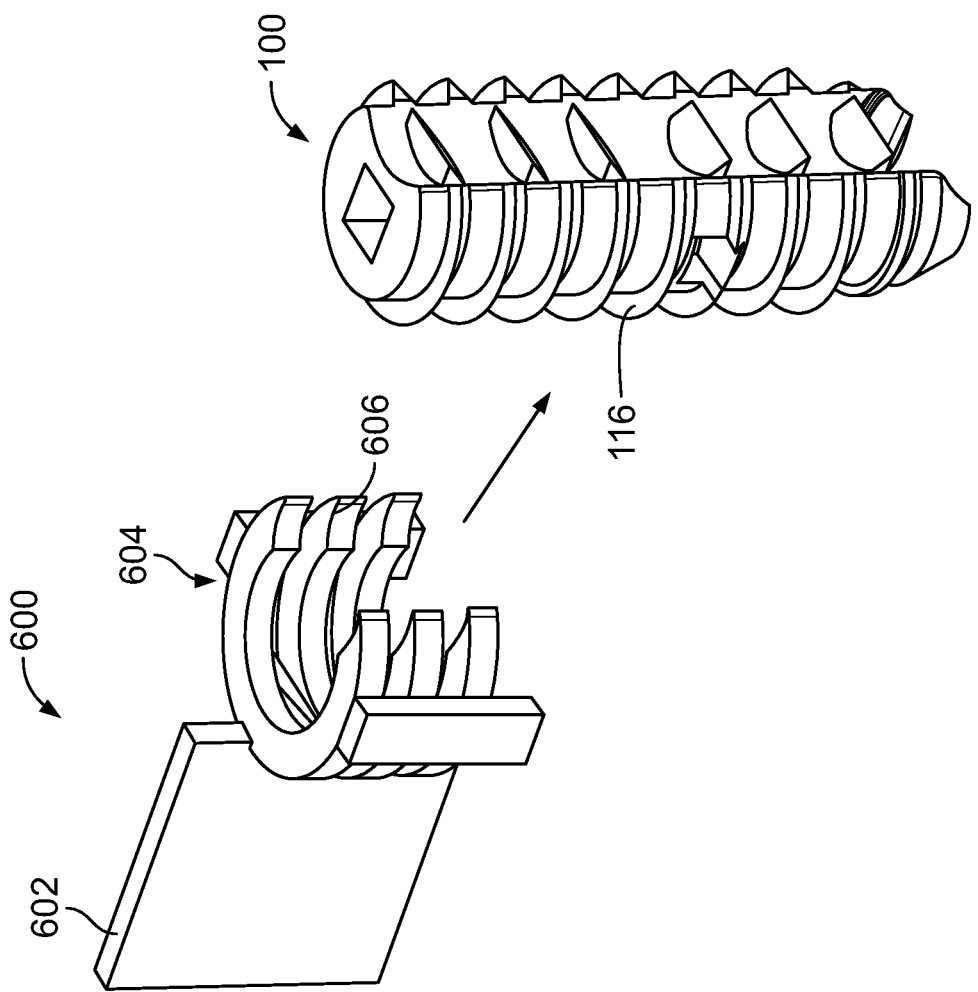
Figures 19, 20:
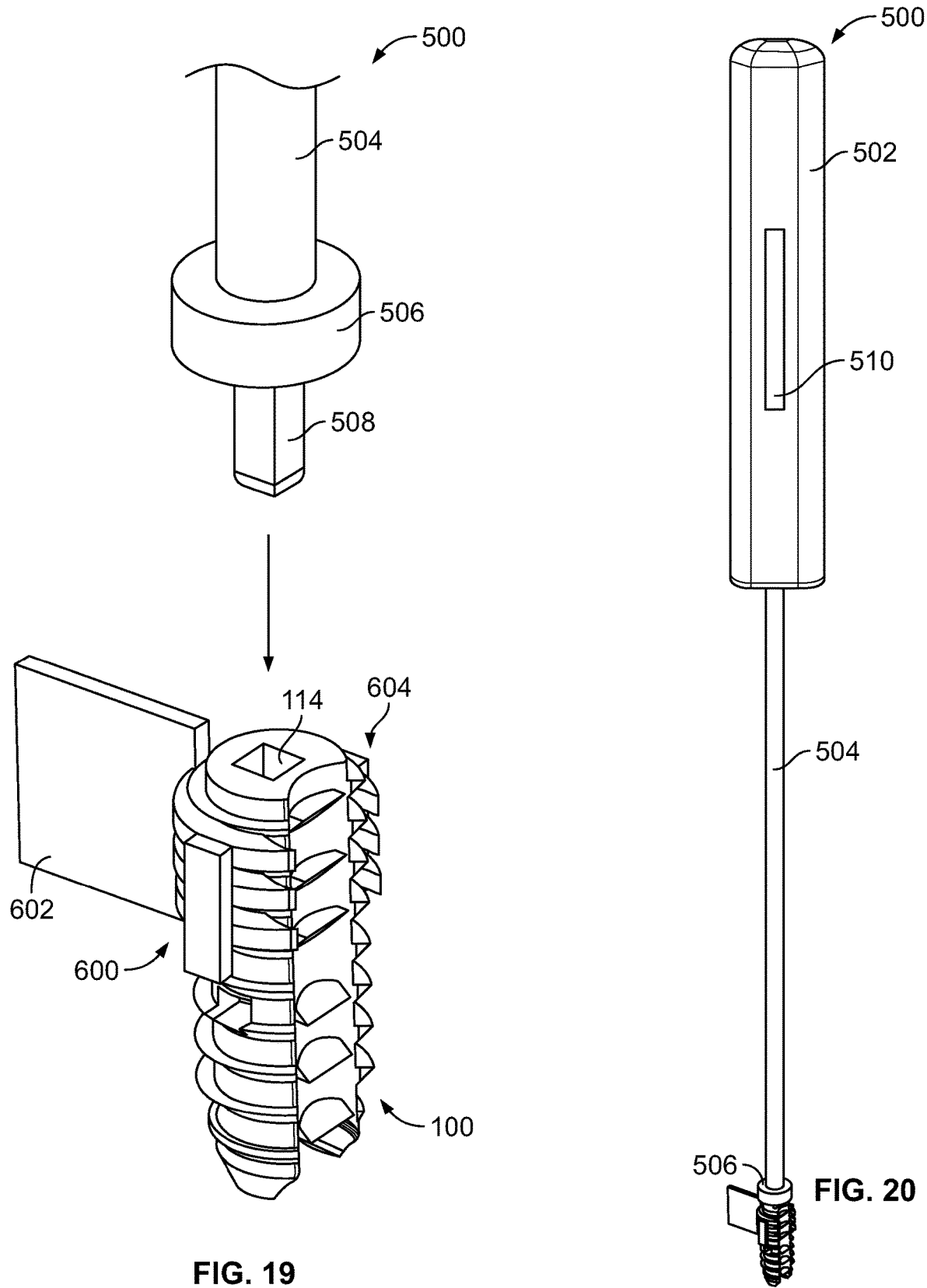

FIGS. 17-20 illustrate a sequence of steps for loading the anchoring device 100 onto the insertion tool 500 (and the illustrated sequence is similarly applicable to the other aforementioned examples of the tendon anchoring devices 200, 300, and 400). As shown in FIGS. 17 and 18, the anchoring device 100 is first coupled to a holder 600 including a support bracket 602 and a gripper 604. The gripper 604 is a claw-like structure including a plurality of outwardly extending figures 606 that fit between the distributed anchor ribs 116 of the anchoring device 100. As shown in FIGS. 19 and 20, the support bracket 602 is used to hold the anchoring device 100 in place as the tip 508 of the insertion tool 500 is introduced to the bore 114 of the device. For example, the support bracket 602 can be held by a human hand or braced by a mechanical device.

FIGS. 21-27 illustrate a sequence of steps for anchoring tendon to bone using the tendon anchoring device 300 and insertion tool 500 described above. (The illustrated sequence is similarly applicable to the other aforementioned examples of the tendon anchoring devices 100, 200, and 400.) The tendon anchoring device used herein can be used to repair a variety of tendons to bone in a variety of different anatomic locations. In a preferred implementation, the tendon anchoring device is used to secure a tendon to a bone in a patient's arm, including for example, anchoring a bicep tendon to bore formed in the targeted bone of the arm. Other examples of securing a tendon to a bone in a patient's arm can include attaching a tendon in the hand, write, elbow to a targeted bone in a respective area.

Figure 21:
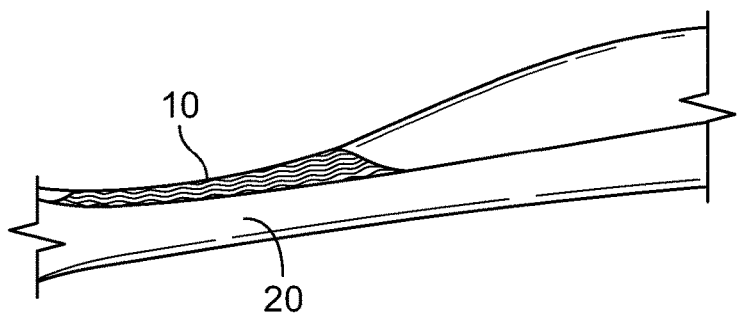
FIGS. 21-27 are progressive diagrams illustrating an example technique for anchoring tendon to bone using a tendon anchoring device.
Figure 22:
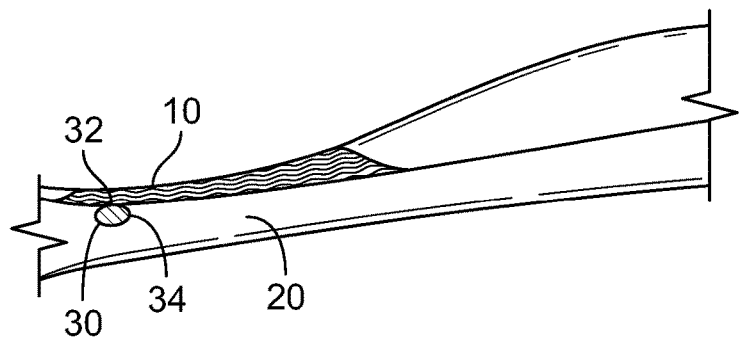

Referring to FIG. 21, a tendon 10 is placed proximate a bone 20 to determine the selected attachment point. Next, as shown in FIG. 22, a tunnel 30 is formed in the bone 20 at the attachment point. The tunnel has an opening 32 and a side wall 34. In this example, the tunnel 30 is a single, circular socket creating a rounded side wall 34. The tunnel 30 can be drilled or punched into the bone 20. A portion of the tendon 10 is then placed over the opening 32 of the tunnel 30.

Figure 23:
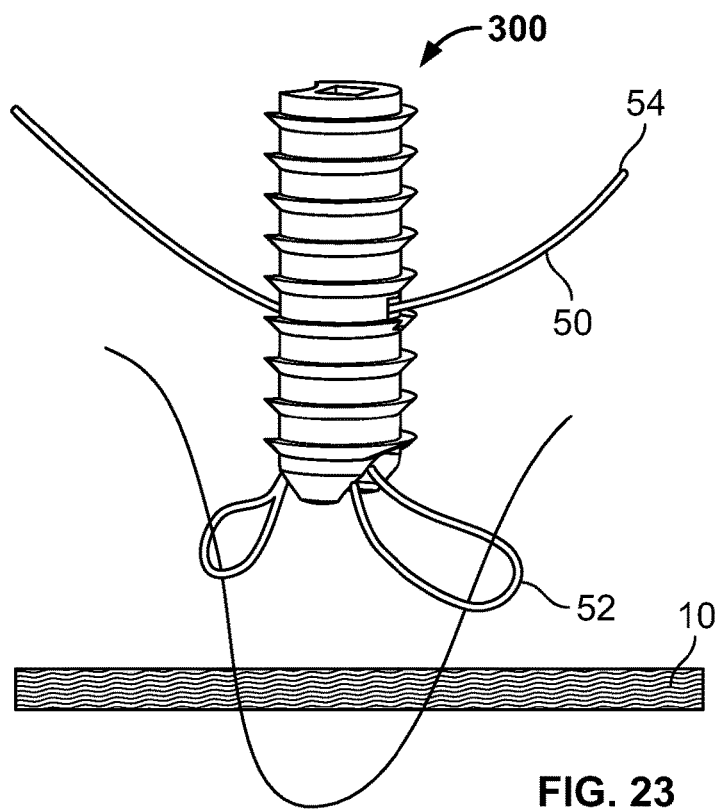
Figure 24:
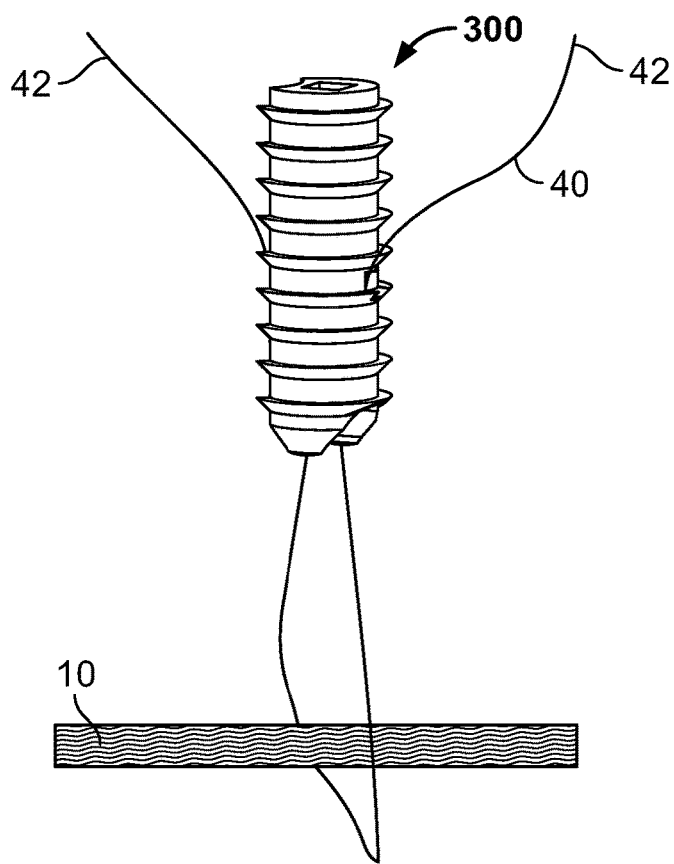
Figure 25:
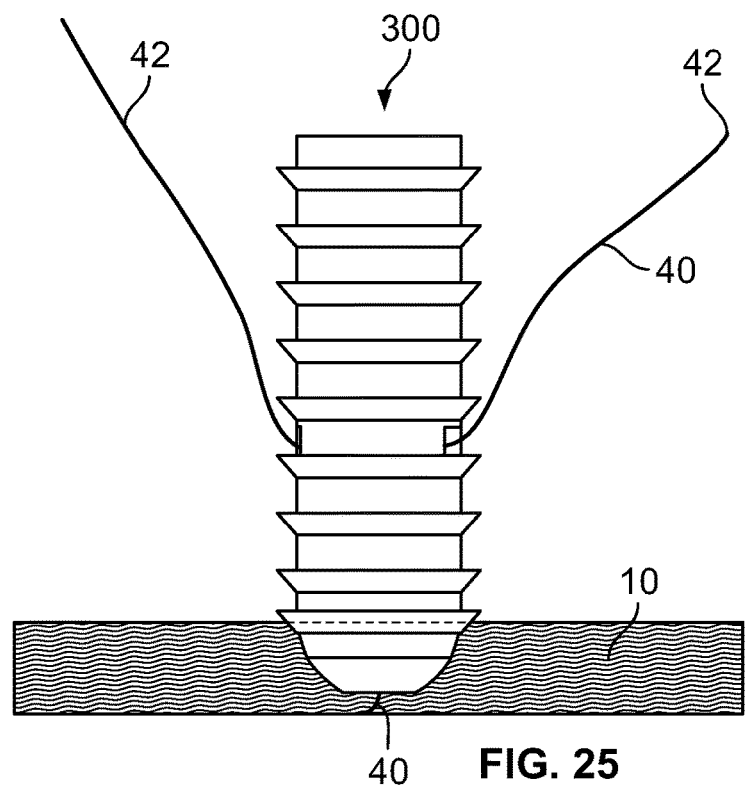
Figure 26:
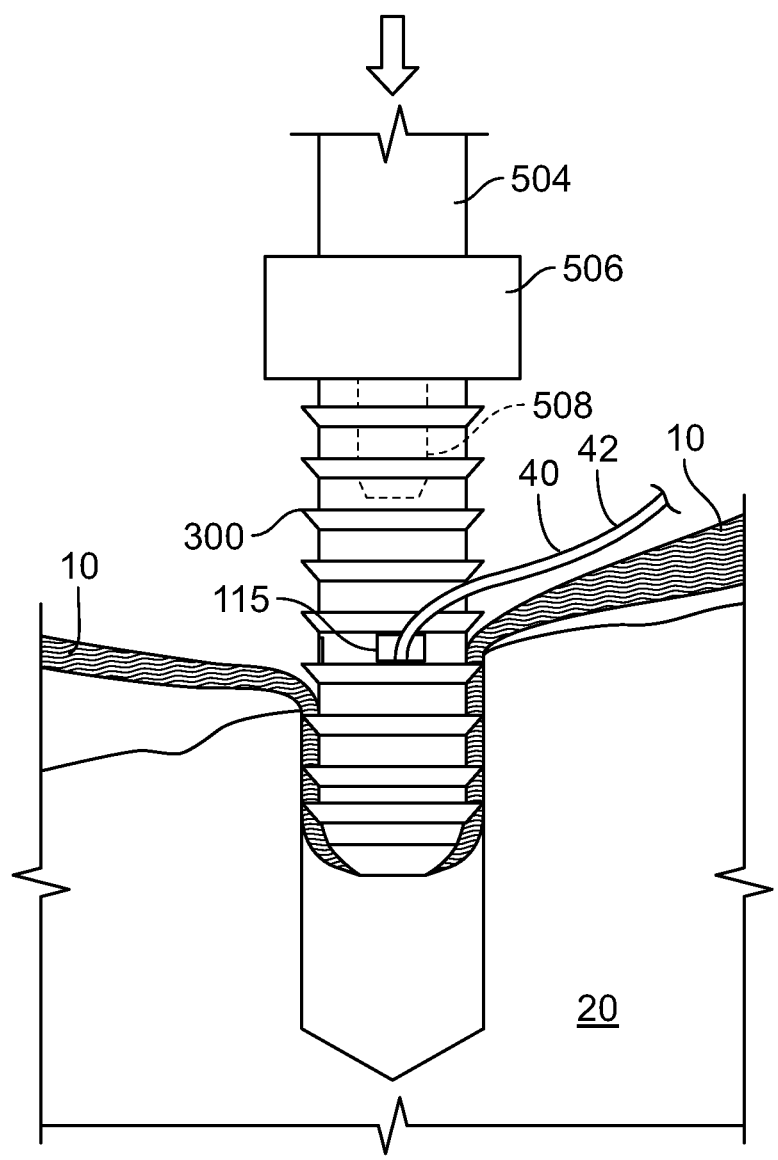
Figure 27:
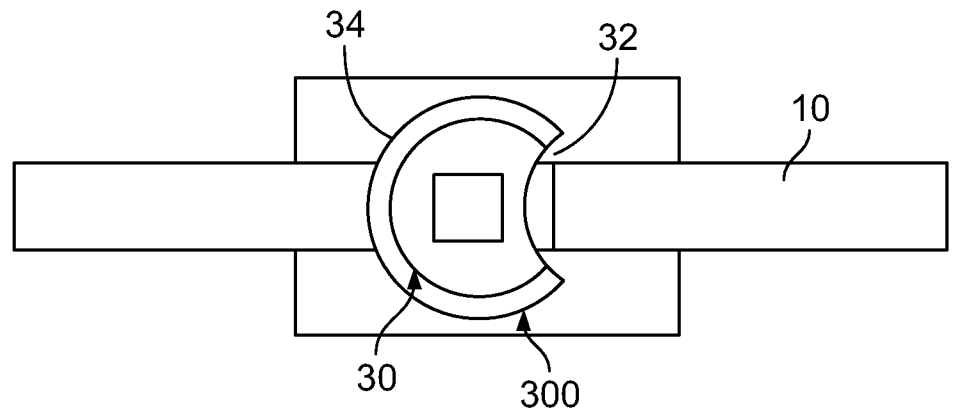

As shown in FIGS. 23-25, the tendon 10 is coupled to the tendon anchoring device 300 by a suture 40 wrapped around the tendon 10 and routed through the anchoring device. In this example, routing of the suture 40 is accomplished using wire loops 50 as "pull-tabs." In some examples, the wire loops 50 are fabricated from a material including nitinol. To implement the pull-tab technique, the two wire loops 50 are inserted through the apertures 115,115' in the convex side wall 110 of the anchoring device 300, fed down through the bore 114, and pulled through the open bottom end 106. This leaves the distal looped ends 52 exposed through the bottom end 106 of the anchoring device 300, and the proximal tab ends 54 exposed through the apertures 115,115' (see FIG. 23). The suture 40 is then routed around the tendon 10 and through the respective looped ends 52. The tab ends 54 are then pulled away from anchoring device 300 to shuttle the ends 42 of the suture 40 through the bore 114 and apertures 115,115' of the device (see FIG. 24). The suture ends 42 are pulled outward to draw the tendon 10 into the archway 126 and against the tendon engagement surface 124 of the anchoring device 300 (see FIG. 25). Once drawn taught, the ends 42 of the suture 40 can be secured to the cleats 510 on the handle of the insertion tool 500 to secure the tendon 10 in place. With the tendon 10 secured, the anchoring device 300 can be forced down into the tunnel 30 by applying a force to the insertion tool 500. Force applied to the insertion tool 500 is transferred to the anchoring device 300 through the flange 506, as discussed above (see FIGS. 26-27). For example, the handle 502 of the insertion tool 500 can be tapped with a mallet to urge the anchoring device 300 and the tendon 10 into the bone tunnel 30. The procedure is then completed by retracting the insertion tool 500 from the bore 114 of the anchoring device 300 and trimming the suture 40.

When the tendon anchoring device 300 is implanted, the tendon 10 extends down along the wall 34 of the tunnel 30, through the archway 126 of the device, and then back up along the tunnel wall 30. As such, the tendon 10 is sandwiched between the wall 34 and the anchoring device 300. The anchor ribs 116 and support ribs 122 engage the tendon 10 to hold it in place against the wall 34 of the tunnel 30. The anchor ribs 116 also directly engage the wall 34 to hold the anchoring device 300 in place absent additional devices, tools, apparatus, bonding agents, or the like. Thus, the tendon anchoring device 300 is said to be "self-anchoring."

Note that the above-described implantation sequence can be performed by a single user (e.g., a surgeon), requiring no more than two hands to: (i) pre-load the tendon anchoring device 300 onto the insertion tool 500; (ii) wrap the suture 40 around the tendon 10 and pass the free ends 42 of the suture 40 through the bore of the anchoring device 300 via the wire loops 50; (iii) draw and hold the tendon 10 in proper engagement with the tendon engagement surface 124 of the device 300 by pulling the ends 42 of the suture 40 and securing them to the cleats 510 of the insertion tool 500; and (iv) force the anchoring device 300 and the tendon 10 into the tunnel 30 formed in the bone 20 by tapping the insertion tool 500 with a mallet. In certain embodiments, step (i) would not need to be performed when the tendon anchoring device 300 is provided in a pre-loaded configuration when provided in a kit form, where the device 300 would be loaded onto the insertion tool 500. In some embodiments, the kit would also include one or more sutures.

Note further that the implantation sequence of FIGS. 21-27 involving anchoring device 300 is merely exemplary and not intended to be limiting. Similar sequences can be used to implant the other anchoring devices discussed herein. For example, the first and second anchoring devices 100,200 could be installed using a single wire loop 50 to shuttle both ends 42 of the suture 40 through the bore 114 and aperture 115 of the devices. Further, in some examples, implantation can be performed without the wire loop(s) 50 and/or without the suture 40. Further deviations from these exemplary embodiments are also contemplated by the present disclosure. For instance, the anchoring device could be provided without the aperture in the convex side wall, and the suture could be introduced to the bore through the opening at the top end of the device.

In some cases, an implantation sequence can be performed without the use of any suturing by a single user (e.g., a surgeon), requiring no more than two hands to: (i) pre-load the tendon anchoring device 300 onto the insertion tool 500;

(ii) hold the tendon 10 in proper engagement with the tendon engagement surface 124 of the device 300 by pinning the tendon within the concave distal tip and moving the tendon in a desired direction; and (iii) force the anchoring device 300 and the tendon 10 into the tunnel 30 formed in the bone 20 by tapping the insertion tool 500 with a mallet.

The use of terminology such as "front," "rear," "top," "bottom," "over," "above," and "below" throughout the specification and claims is for describing the relative positions of various components of the system and other elements described herein. Similarly, the use of any horizontal or vertical terms to describe elements is for describing relative orientations of the various components of the system and other elements described herein. Unless otherwise stated explicitly, the use of such terminology does not imply a particular position or orientation of the system or any other components relative to the direction of the Earth gravitational force, or the Earth ground surface, or other particular position or orientation that the system other elements may be placed in during operation, manufacturing, and transportation.

A number of embodiments of the invention have been described. Nevertheless, it will be understood that various modifications may be made without departing from the scope of the inventions.

The invention claimed is:

1. A tendon anchoring device, comprising:
   an elongated body extending between a first end and a second end, the body comprising at least one concave side wall and at least one convex side wall, the concave and convex side walls extending longitudinally between the first and second ends;
   a tool engagement surface at the first end of the body adapted to accommodate a mating surface of an insertion tool;
   a tendon engagement surface at the second end of the body, the tendon engagement surface defining an archway bounded by overhanging portions of the convex side wall;
   a plurality of anchor ribs projecting laterally from the convex side wall and distributed between the first and second ends of the body, each of the anchor ribs engageable with a wall formed along a tunnel of a bone; and
   a plurality of support ribs projecting laterally from the concave side wall and distributed between the first and second ends of the body, each of the support ribs engageable with a tendon residing within the archway of the tendon engagement surface, wherein one or more of the plurality of support ribs are longitudinally canted relative to a transverse plane of the body, wherein a first set of the support ribs are canted at a first angle relative to the transverse plane and a second set of the support ribs are canted at a second angle that is different from the first.

2. The tendon anchoring device of claim 1, wherein the concave side wall is contiguous to the convex side wall, the concave and convex sidewalls defining the lateral boundary of the body.

3. The tendon anchoring device of claim 1, wherein the convex side wall defines a substantially circular cross-section.

4. The tendon anchoring device of claim 1, wherein the tendon engagement surface meets the concave side wall at a first arcuate edge, and wherein the archway extends across the body to meet a portion of the convex side wall at a second arcuate edge.

5. The tendon anchoring device of claim 1, wherein the body further comprises an interior throughbore extending between the first and second ends of the body.

6. The tendon anchoring device of claim 5, wherein the throughbore is sized to receive at least a portion of a suture thread.

7. The tendon anchoring device of claim 5, wherein the throughbore extends from an opening at the first end of the body, the opening shaped to accommodate a portion of the insertion tool in an interlocking engagement.

8. The tendon anchoring device of claim 5, wherein the throughbore defines a rectangular cross-section.

9. The tendon anchoring device of claim 5, wherein the throughbore comprises no more than 20% of the cross-sectional area of the body.

10. The tendon anchoring device of claim 1, wherein at least one of the anchor ribs comprises an annular, inverse-frustum-shaped structure circumscribing the convex side wall.

11. The tendon anchoring device of claim 1, wherein the plurality of anchor ribs are spaced apart from one another at regular intervals along the convex side wall.

12. The tendon anchoring device of claim 1, wherein the body further comprises an aperture located on the convex side wall sized to receive at least a portion of a suture thread.

13. The tendon anchoring device of claim 12, wherein the aperture extends through the convex side wall to intersect a longitudinal interior throughbore of the body.

14. The tendon anchoring device of claim 12, wherein the body comprises first and second apertures aligned on opposing locations of the convex side wall to form a passageway extending across the body.

15. The tendon anchoring device of claim 1, wherein the body comprises an integral, monolithic structure comprising a material selected from the group consisting of: poly ether ether ketone, poly-L-lactic acid, titanium, and stainless steel.

16. A tendon anchoring device, comprising:
   an elongated body extending between a first end and a second end, the body comprising at least one concave side wall and at least one convex side wall, the concave and convex side walls extending longitudinally between the first and second ends;
   a tool engagement surface at the first end of the body adapted to accommodate a mating surface of an insertion tool;
   a tendon engagement surface at the second end of the body, the tendon engagement surface defining an archway bounded by overhanging portions of the convex side wall;
   a plurality of anchor ribs projecting laterally from the convex side wall and distributed between the first and second ends of the body, each of the anchor ribs engageable with a wall formed along a tunnel of a bone; and
   a plurality of support ribs projecting laterally from the concave side wall and distributed between the first and second ends of the body, each of the support ribs engageable with a tendon residing within the archway of the tendon engagement surface, wherein the concave side wall constitutes the only concave portion of the lateral boundary of the body.

17. A method for coupling a tendon to a bone, the method comprising:
   forming a tunnel in a bone, the tunnel comprising an opening and a wall circumscribing the opening;
   placing a tendon over the opening of the tunnel;

placing a tendon anchoring device over the opening and at least a portion of the tendon, the anchoring device comprising:
- an elongated body comprising at least one concave side wall and at least one convex side wall extending longitudinally between first and second ends of the body;
- a tool engagement surface at the first end of the body;
- a tendon engagement surface at the second end of the body, the tendon engagement surface defining an archway bounded by overhanging portions of the convex side wall;
- a plurality of anchor ribs projecting laterally from the convex side wall; and
- a plurality of support ribs projecting laterally from the concave side wall, wherein one or more of the plurality of the support ribs of the anchoring device are longitudinally canted relative to a transverse plane of the body, wherein a first set of the support ribs are canted at a first angle relative to the transverse plane and a second set of the support ribs are canted at a second angle that is different from the first;

aligning the tendon engagement surface with the tendon to place the tendon within the archway; and placing the anchoring device carrying the tendon into the tunnel through the opening, thereby causing the anchor ribs to engage the wall of the tunnel and the support ribs to support the tendon against the wall of the tunnel.

18. The method of claim 17, wherein the concave side wall of the anchoring device is contiguous to the convex side wall, the concave and convex sidewalls defining the lateral boundary of the body.

19. The method of claim 17, wherein the convex side wall of the anchoring device defines a substantially circular cross-section.

20. The method of claim 17, wherein the tendon engagement surface of the anchoring device meets the concave side wall at a first arcuate edge, and wherein the archway extends across the body to meet a portion of the convex side wall at a second arcuate edge.

21. The method of claim 17, wherein the body of the anchoring device further comprises an interior throughbore extending between the first and second ends of the body.

22. The method of claim 21, wherein the throughbore is sized to receive at least a portion of a suture thread.

23. The method of claim 21, wherein the throughbore extends from an opening at the first end of the body, the opening shaped to accommodate a portion of the insertion tool in an interlocking engagement.

24. The method of claim 21, wherein the throughbore defines a rectangular cross-section.

25. The method of claim 21, wherein the throughbore comprises no more than 20% of the cross-sectional area of the body.

26. The method of claim 17, wherein at least one of the anchor ribs of the anchoring device comprises an annular, inverse-frustum-shaped structure circumscribing the convex side wall.

27. The method of claim 17, wherein the plurality of anchor ribs of the anchoring device are spaced apart from one another at regular intervals along the convex side wall.

28. The method of claim 17, wherein aligning the tendon engagement surface with the tendon comprises:
- routing a suture thread through at least a portion of an interior bore of the body of the anchoring device; and
- routing the suture thread around the tendon.

29. The method of claim 28, wherein routing the suture thread through the interior bore comprises inserting the suture thread through an opening at the tool engagement surface of the anchoring device.

30. The method of claim 28, wherein routing the suture thread through the interior bore comprises inserting the suture thread through an opening at the convex side wall of the anchoring device.

31. The method of claim 28, wherein aligning further comprises: pulling two opposing end portions of the suture thread to urge the tendon against the tendon engagement surface.

32. The method of claim 28, further comprising, prior to forcing the anchoring device into the tunnel, securing the suture thread to a cleat located on an insertion tool coupled to the anchoring device.

33. The method of claim 17, wherein placing the anchoring device into the tunnel comprises:
- engaging an insertion tool with the anchoring device by:
  - placing a tip of the insertion tool within an interior bore of the anchoring device; and
  - placing a flange of the insertion tool against the tool engagement surface of the anchoring device; and
- applying a force to the insertion tool.

34. A method for coupling a tendon to a bone, the method comprising:
forming a tunnel in a bone, the tunnel comprising an opening and a wall circumscribing the opening;
placing a tendon over the opening of the tunnel;
placing a tendon anchoring device over the opening and at least a portion of the tendon, the anchoring device comprising:
- an elongated body comprising at least one concave side wall and at least one convex side wall extending longitudinally between first and second ends of the body;
- a tool engagement surface at the first end of the body;
- a tendon engagement surface at the second end of the body, the tendon engagement surface defining an archway bounded by overhanging portions of the convex side wall;
- a plurality of anchor ribs projecting laterally from the convex side wall; and
- a plurality of support ribs projecting laterally from the concave side wall;

aligning the tendon engagement surface with the tendon to place the tendon within the archway; and placing the anchoring device carrying the tendon into the tunnel through the opening, thereby causing the anchor ribs to engage the wall of the tunnel and the support ribs to support the tendon against the wall of the tunnel, wherein the concave side wall of the anchoring device constitutes the only concave portion of the lateral boundary of the body.

35. A surgical kit, comprising:
a tendon anchoring device comprising:
an elongated body extending between a first end and a second end, the body comprising at least one concave side wall and at least one convex side wall, the concave and convex side walls extending longitudinally between the first and second ends;
a tool engagement surface at the first end of the body;
a tendon engagement surface at the second end of the body, the tendon engagement surface defining an archway bounded by overhanging portions of the convex side wall;

a plurality of anchor ribs projecting laterally from the convex side wall and distributed between the first and second ends of the body, each of the anchor ribs engageable with a wall formed along a tunnel of a bone; and a plurality of support ribs projecting laterally from the concave side wall and distributed between the first and second ends of the body, each of the support ribs engageable with a tendon residing within the archway of the tendon engagement surface, wherein one or more of the plurality of the support ribs of the anchoring device are longitudinally canted relative to a transverse plane of the body, wherein a first set of the support ribs are canted at a first angle relative to the transverse plane and a second set of the support ribs are canted at a second angle that is different from the first; and an insertion tool adapted to interface with the tool engagement surface of the anchoring device and facilitate insertion of the anchoring device into the tunnel of the bone.

36. The surgical kit of claim 35, wherein the concave side wall of the anchoring device is contiguous to the convex side wall, the concave and convex sidewalls defining the lateral boundary of the body.

37. The surgical kit of claim 35, wherein the convex side wall of the anchoring device defines a substantially circular cross-section.

38. The surgical kit of claim 35, wherein the tendon engagement surface of the anchoring device meets the concave side wall at a first arcuate edge, and wherein the archway extends across the body to meet a portion of the convex side wall at a second arcuate edge.

39. The surgical kit of claim 35, wherein the body of the anchoring device further comprises an interior throughbore extending between the first and second ends of the body.

40. The surgical kit of claim 39, wherein the throughbore is sized to receive at least a portion of a suture thread.

41. The surgical kit of claim 39, wherein the throughbore extends from an opening at the first end of the body, the opening shaped to accommodate a portion of the insertion tool in an interlocking engagement.

42. The surgical kit of claim 39, wherein the throughbore defines a rectangular cross-section.

43. The surgical kit of claim 39, wherein the throughbore comprises no more than 20% of the cross-sectional area of the body.

44. The surgical kit of claim 35, wherein at least one of the anchor ribs of the anchoring device comprises an annular, inverse-frustum-shaped structure circumscribing the convex side wall.

45. The surgical kit of claim 35, wherein the plurality of anchor ribs of the anchoring device are spaced apart from one another at regular intervals along the convex side wall.

46. The surgical kit of claim 35, wherein the body of the anchoring device further comprises an aperture located on the convex side wall sized to receive at least a portion of a suture thread.

47. The surgical kit of claim 46, wherein the aperture extends through the convex side wall to intersect a longitudinal interior throughbore of the body.

48. The surgical kit of claim 46, wherein the body comprises first and second apertures aligned on opposing locations of the convex side wall to form a passageway extending across the body.

49. The surgical kit of claim 35, wherein the body of the anchoring device comprises an integral, monolithic structure comprising a material selected from the group consisting of: poly ether ether ketone, poly-L-lactic acid, titanium, and stainless steel.

50. The surgical kit of claim 35, wherein the insertion tool comprises a cleat for securing a suture thread wrapped around a tendon and the anchoring device.

51. The surgical kit of claim 35, wherein the anchoring device comprises an interior throughbore extending between the first and second ends of the body, and wherein the insertion tool comprises a tip configured to engage the interior throughbore to couple the insertion tool to the anchoring device.

52. The surgical kit of claim 51, wherein the tip of the insertion tool and the throughbore of the anchoring device are configured to provide an interlocking engagement.

53. The surgical kit of claim 51, wherein the tip of the insertion tool has a rectangular cross-section.

54. The surgical kit of claim 35, wherein the insertion tool comprises a flange for interfacing with the tool engagement surface of the anchoring device, the interface sufficient to transfer force applied to the insertion tool to the anchoring device.

55. The surgical kit of claim 54, wherein the lateral boundary of the flange is larger than that of the tool engagement surface.

56. A surgical kit, comprising:
a tendon anchoring device comprising:
an elongated body extending between a first end and a second end, the body comprising at least one concave side wall and at least one convex side wall, the concave and convex side walls extending longitudinally between the first and second ends;
a tool engagement surface at the first end of the body;
a tendon engagement surface at the second end of the body, the tendon engagement surface defining an archway bounded by overhanging portions of the convex side wall;
a plurality of anchor ribs projecting laterally from the convex side wall and distributed between the first and second ends of the body, each of the anchor ribs engageable with a wall formed along a tunnel of a bone; and
a plurality of support ribs projecting laterally from the concave side wall and distributed between the first and second ends of the body, each of the support ribs engageable with a tendon residing within the archway of the tendon engagement surface; and
an insertion tool adapted to interface with the tool engagement surface of the anchoring device and facilitate insertion of the anchoring device into the tunnel of the bone, wherein the concave side wall of the anchoring device constitutes the only concave portion of the lateral boundary of the body.

57. A tendon anchoring device, comprising:
a body extending between a first end and a second end, the body comprising a concave side wall and a convex side wall, the concave and convex side walls extending between the first and second ends, wherein the concave side wall constitutes the only concave portion of the lateral boundary of the body;
a tool engagement surface at the first end of the body;
a tendon engagement surface at the second end of the body;
a plurality of anchor ribs projecting from the convex side wall and distributed between the first and second ends of the body; and a plurality of support ribs projecting from the concave side wall and distributed between the first and second ends of the body.

\* \* \* \* \*